Figure 1:
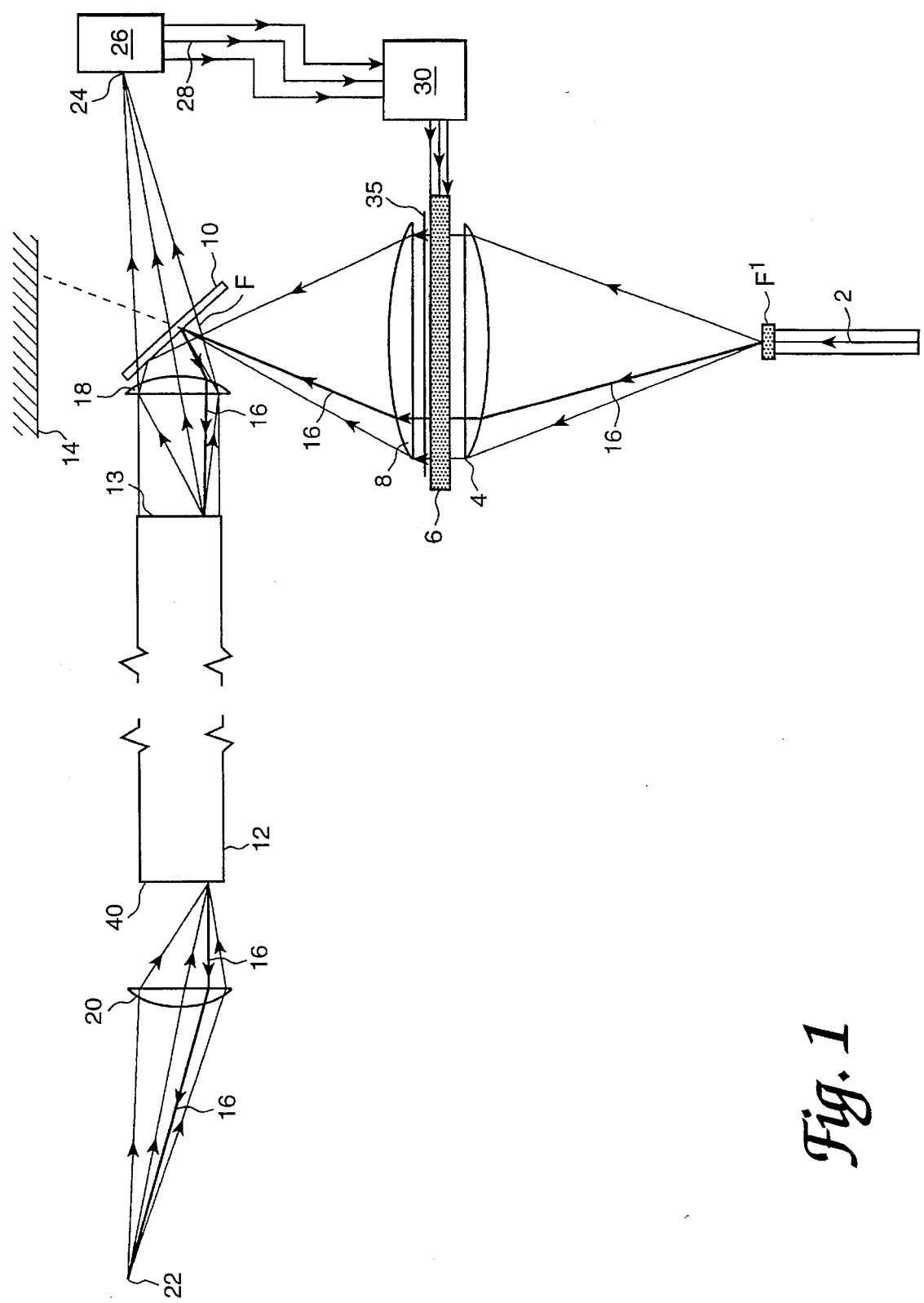

United States Patent [19]

Shanks

[11] Patent Number: 5,514,127
[45] Date of Patent: May 7, 1996

[54] APPARATUS FOR IRRADIATING AN AREA WITH A CONTROLLABLE PATTERN OF LIGHT

[75] Inventor: Ian A. Shanks, Penn, Great Britain

[73] Assignee: Central Research Laboratories Limited, Middlesex, England

[21] Appl. No.: 198,063

[22] Filed: Feb. 18, 1994

[30] Foreign Application Priority Data

Feb. 18, 1993 [GB] United Kingdom .................... 9303261
Apr. 30, 1993 [GB] United Kingdom .................... 9308977

[51] Int. Cl.⁶ ........................................................ A61B 6/00
[52] U.S. Cl. ................................ 606/10; 606/16; 606/14
[58] Field of Search ................................. 606/10, 11, 12, 606/4, 5, 6; 364/413.14, 413.23; 356/398, 392, 393, 394, 125, 51; 128/4

[56] References Cited

U.S. PATENT DOCUMENTS

| | | | |
|---|---|---|---|
| 4,443,075 | 4/1984 | Crane | 606/4 |
| 4,612,938 | 9/1986 | Dietrich et al. | 128/665 |
| 4,917,486 | 4/1990 | Raven et al. | 606/4 |
| 4,987,410 | 1/1991 | Berman et al. | 340/705 |
| 5,054,888 | 10/1991 | Jacobs et al. | 359/76 |
| 5,325,218 | 6/1994 | Willett et al. | 359/53 |
| 5,350,374 | 9/1994 | Smith | 606/5 |
| 5,377,036 | 12/1994 | Appel et al. | 359/216 |

*Primary Examiner*—Stephen C. Pellegrino
*Assistant Examiner*—Sonya Harris-Ogugua
*Attorney, Agent, or Firm*—Keck, Mahin & Cate

[57] ABSTRACT

Apparatus for irradiating an area with a controllable pattern of light comprises a laser (2), which illuminates a spatial light modulator (6). The resulting spatially modulated light then passes to a cholesteric liquid crystal polymer beamsplitter (10) which reflects it to an image surface (13) of an endoscope (12). The endoscope relays it to another image surface (40) whence it is focussed on the area to be irradiated. This light may be used for photodynamic therapy.

9 Claims, 2 Drawing Sheets

APPARATUS FOR IRRADIATING AN AREA WITH A CONTROLLABLE PATTERN OF LIGHT

The present invention relates to an apparatus for irradiating an area with a controllable pattern of light. The invention has particular, although not exclusive relevance to supplying light to a treatment area.

It is known to utilise laser light to perform photodynamic therapy. In such therapy growths or tumours are killed-off in a patient who has received a material which can cause a phototoxic effect by selectively irradiating the growth with moderate-intensity light of appropriate wavelengths. This is achieved by rendering the area of tissue (the treatment area) within which the growth is situated photo-sensitive such that such irradiation causes a non-toxic chemical to form a toxic material which will kill the growth tissue. The required dosage of light varies over the area to be treated according to the prevalence or thickness of the growth and so some form of control of this light is necessary.

EP-A-0,194,856 discloses a system for performing such therapy in which optical fibres are inserted into, e.g. an artery and are arranged such that the distal end of the fibres will irradiate an area containing a growth to be removed, the proximal end of the fibres communicating with a treatment laser via a light modulator and a beam-splitter. The fibres may be used in conjunction with, or be part of, an endoscope used to view the treatment area. The modulator is arranged selectively to interrupt passage of the laser light to the fibres and the beam-splitter is situated intermediate the modulator and the fibres in order to "tap-off" a portion of the light to ensure constancy of the amplitude of the laser over time. The fibres are also arranged to transmit light from a further, diagnostic light source in order to flood the growth with light in order that the progress of the treatment may be monitored. This is achieved by the fibres also being able to transmit reflected or emitted light from a fluorescent dye or label which has selectively accumulated in the growth area, via a light coupler to a detector device able to control the output of the treatment laser. In this way, once the growth has been removed, the light sent via the fibres from the growth site to the detector device is negligible (being only reflected from the treatment area when the growth is present) and so the output of the treatment laser is stopped.

The known system suffers from the disadvantage however that there is no facility for controlling which parts of the treatment area, corresponding to the area only of the growth itself, are to be illuminated and with what dosage. Either the whole of the treatment area is illuminated by that part of the fibre which is optically coupled to the treatment laser, or it is not. This can result in the overtreatment of some regions and the undesirable or fatal destruction of healthy tissue. Thus in order effectively to remove the growth, the area of illumination of the fibre must be sufficiently small that the fibre can be steered or swept over the growth by a practitioner in order to completely irradiate the growth. This requires considerable coordination and skill and still leaves scope for inadvertent damage to healthy tissue in surrounding area. It is also a slow procedure if adequate care is used.

It is an object of the present invention to alleviate these shortcomings.

The invention provides apparatus for irradiating an area with a controllable pattern of light, comprising an endoscope for relaying an image between first and second image surfaces and a system for selectively directing light onto a given area of one of the image surfaces to thereby selectively irradiate a corresponding area of the other of the image surfaces, said system including a source for the light, a beam splitter in a path for the light from the source to said one of the image surfaces for diverting at least a portion of any light returning from said one of the image surfaces out of said path, and means for variably controlling the given area onto which the light is selectively directed.

By variable controlling the given area onto which the light is selectively directed, and hence the pattern of light which is ultimately produced at, for example, a treatment area, the need for a practitioner to actually sweep the light emanating from the endoscope, for example over a growth, can be obviated, thereby minimising the possibility of damaging healthy tissue while enhancing the ease and speed of treatment.

Preferably the beam splitter comprises a sheet of cholesteric liquid crystal material tilted at an angle to said path for reflecting at least a portion of light from the source to said one of the image surfaces and transmitting at least a portion of any light returning from said one of the image surfaces. An advantage of utilising cholesteric liquid crystal material is that a high degree of optical efficiency may be achieved.

Figure 2:
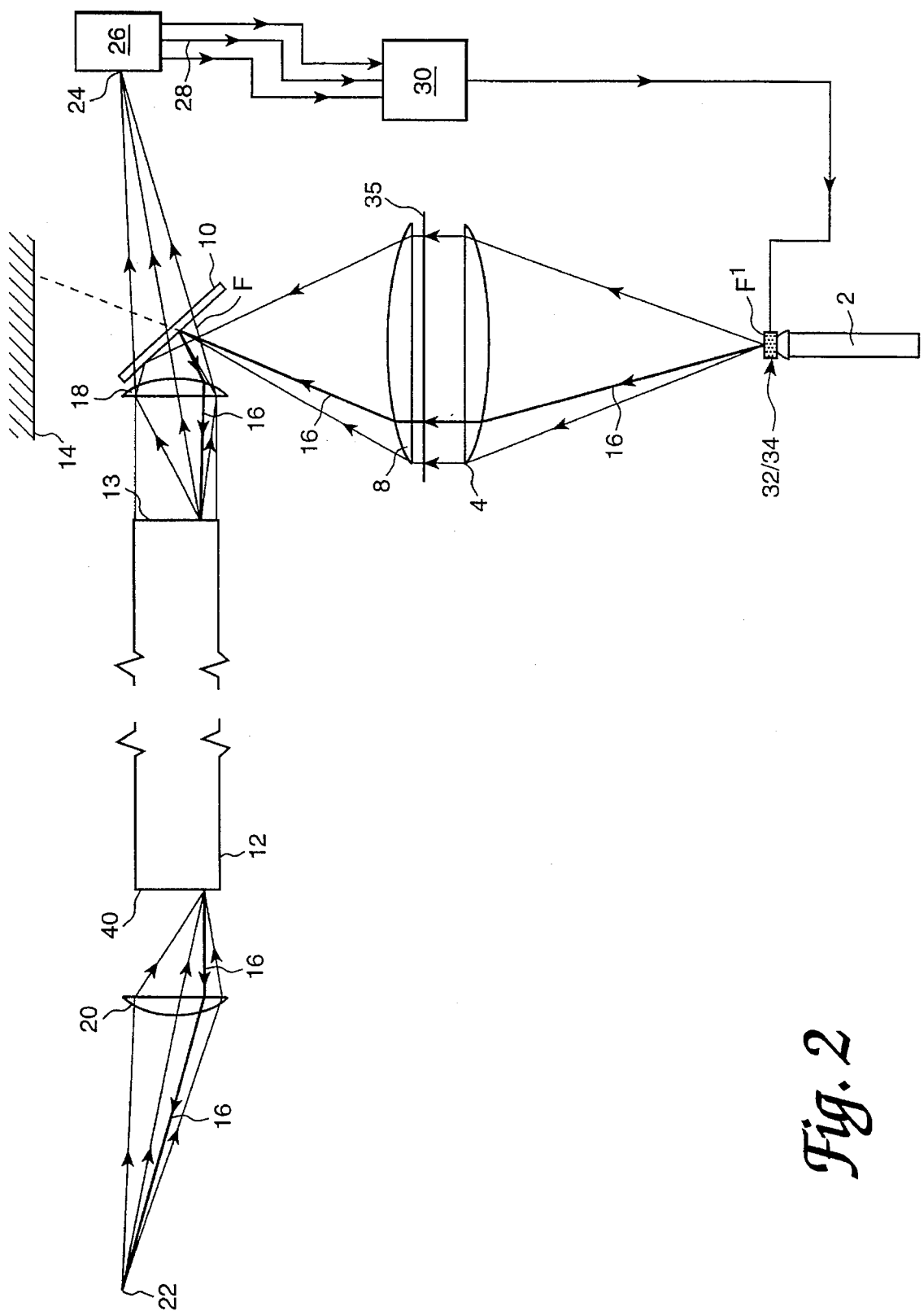

The invention will now be described, by way of example only, with reference to the accompanying diagrammatic drawings in which FIG. 1 shows a first embodiment and FIG. 2 shows a second embodiment.

Each embodiment may be used for photodynamic therapy in a patient treated systemically with 5-aminolevullinic acid which has metabolised to create a high concentration of protoporphyrin IX in the growth.

A light source, in the example a HeNe red laser 2, (632.8 mm) 1 to 10 watts power output continuous wave, with linear polarisation, emits light which is focussed at F1 and thereafter illuminates a beam expander lens 4. On the opposite of the beam expander lens 4 to the laser 2 is a spatial light modulator, in this example a liquid crystal display (LCD) 6 comprising a matrix array (say 100×100) of pixels each individually variable between first and second light transmission states which overall result in light transmission and light non-transmission respectively. This property may be achieved directly. Alternatively the states may be, for example, different polarisation states which are subsequently analysed.

The beam expansion is provided so that the light from the laser 2 floods the whole of the area of the LCD 6 occupied by the matrix of pixels. By such an arrangement, the resolution afforded by the LCD 6 when operating on the light from the laser is enhanced compared to a case when no beam expanding arrangement is used and therefore the light modulator would have to occupy an area corresponding only to an area which could be directly illuminated by the laser 2 and would have tiny pixels which were difficult/costly to define and could give unwanted diffraction effects and electrical connection difficulties.

On the other side of LCD 6 is a beam condenser 8 and a quarter wave retarder 35 which converts the linearly polarised light incident thereon to either right or left-handed circularly polarised light.

Light from laser 2 focussed at $F^1$ and then travelling through the beam expander/condenser (4,8) and the LCD 6 and the quarter wave retarder 35 comes to a focus and then impinges upon a beam-splitter 10 comprising a sheet of cholesteric liquid crystal material, in this example "LC-Silicone CC 3767 (red) SJ 138/6" manufactured by Wacker. The beam-splitter 10 is arranged at an angle to the beam of light impinging thereupon, this angle being such that at least some of the light impinging upon the beam-splitter 10 is reflected towards an endoscope 12, any remainder being transmitted through the beam-splitter 10 to an optical absorber 14.

The cholesteric liquid crystal polymer imparts to the beam-splitter 10 the optical properties that the portion of light impinging hereupon which is reflected will be of only a narrow wavelength range (e.g. 20 nm to 100 nm.) Furthermore, the polymer will only reflect light having a certain polarisation characteristic, namely either left- or right-handed circular polarisation. The polymer is chosen such that the wavelength range and polarisation state reflected match those of the laser light emerging from the quarter wave retarder 35, any remaining of the light will be transmitted by the beam-splitter 10.

Considering now the operation of the above-described apparatus in more detail with particular reference to ray-trace 16 originating from laser 2, it can be seen that this ray 16 passes through the left-hand portion of LCD 6 and the quarter wave retarder 35. Due to the beam condenser 8 this ray 16 will pass through the focus F and impinge upon the beam-splitter 10 at its lower portion and, assuming the wavelength of ray 16 matches that of the reflection spectrum for the beam-splitter 10, will be reflected to a point on the proximal end of endoscope 12. The ray 16 enters the lower portion of the endoscope 12 at an image surface 13 via lens 18 and hence exits also from the lower portion of endoscope 12 at an image surface 40 (assuming that optical fibres comprising the endoscope 12 are a coherent bundle and have not been axially twisted). The ray 16 is then, via lens 20, deflected to arrive at the corresponding treatment area 22.

Thus the ray 16 having passed through the LCD 6 on the left hand side thereof has also been brought to an area, in this example a treatment area 22, also at the left hand side thereof. In this way, therefore, by controlling which pixels of the LCD 6 are appropriately transmissive or non-transmissive or a state therebetween, then the corresponding controllable light pattern is supplied to the endoscope 12 and thus to the treatment area 22. Hence, for example, an area of LCD 6 may be rendered transmissive corresponding to an area occupied by a malignant growth at treatment area 22.

The circularly polarised light which is focussed at treatment area 22 will, at least to some extent, be scattered and depolarised by the surface which it strikes. Some, at least, of this depolarised light will enter the endoscope 12 again, via lens 20 and exit the endoscope to pass through lens 18 and impinge upon the beam-splitter 10 from the side thereof adjacent lens 18. All except the relevant circular polarisation component of this unpolarised light will be transmitted by the beam-splitter and brought to a focus at further image area 24. An observer beyond 24 will thus be able to view the treatment area 22 e.g. via an eyepiece lens. It will be apparent that because the light brought to a focus at further image area 24 has been transmitted (as opposed to reflected) by the beam-splitter 10, then the aforementioned wavelength-selective effects are no longer present to a significant degree. Hence the observer viewing beyond further area 24 will see essentially all wavelengths of light which are present at the treatment area 22. An optical imaging means, in this example a camera 26, is located to view image area 24 and hence the treatment area 22. The camera 26 has an output 28 which is input to a control means, in this example an image analysis computer 30, which is able to control the optical transmissivity state of each of the pixels within LCD 6. In this way the exact area to be irradiated at treatment area 22 may be determined by the pixels of the LCD 6 under the control of the image analysis computer 30 which receives its input from the camera 26 viewing treatment area 22. Thus an iterative optical control process may be implemented such that when, say, a malignant growth at treatment area 22 has been removed, it can no longer be viewed by camera 26 and so the corresponding pixels of LCD 6 are set to their totally non-transmissive state. However, those skilled in the art will realise that camera 26 and image analysis computer 30 are not essential; the LCD 6 may also be set manually by, for example configuring its pattern of pixel transmissivities using an overlay of the LCD 6 layout on the image viewed on a monitor or directly through an eyepiece. The endoscope 12 may comprise, for example, a coherent bundle of optical fibres or a plurality of eye-glass lenses held rigidly in lines along the length of a tube. In either case, there will be a 1:1 image correlation between the distal and the proximal ends.

Although in the above description, an LCD 6 (in which the liquid crystal material may be ferroelectric) has been given a an example of a spatial light modulator, it will be appreciated that there are various efficacious alternatives, for example a dot matrix array or the like.

The pixels in the spatial light modulator, in addition to controlling the pattern of light passed thereby may control the intensity of this light independently for each pixel.

Although the above example has described the spatial light modulator as being an LCD 6 which is comprised of individually switchable pixels, each switchable between either a light transmissive or non-transmissive state, there are other options available. Because the beam-splitter 10 comprises cholesteric liquid crystal, and an inherent property of such material, as has been hereinbefore described, is to reflect light incident thereon only of a certain sense of circular polarisation, then if the pixels of the spatial light modulator were to be switched variably between, say, two orthogonal states of polarisation (one being matched to the sense reflected by the cholesteric liquid crystal), instead of being switched between either a light transmissive or a non-transmissive state, this provides a further way of supplying a controllable pattern of light to the endoscope 12. This is because those areas of the pattern defined by pixels within the spatial light modulator not switched so as to impart to the light transmitted therethrough the sense of polarisation reflected by the cholesteric liquid crystal will be "dark" when entering the endoscope 12, because within these areas, no light has been reflected by the beam-splitter 10. In such a case the beam-splitter 10 effectively acts as an optical analyser of the output of the spatial light modulator.

Referring now also to FIG. 2, in which an alternative arrangement to that of FIG. 1 is illustrated and in which like components are similarly referenced, it can be seen that the LCD 6 has been omitted. In some circumstances this may be desirable because, whilst the LCD 6 provides direct modulation of light striking the beamsplitter 10, those pixels of the matrix of the LCD 6 which are set into their non-transmissive mode will obviously cause some optical loss, and therefore a reduction in the efficiency of the system. Hence, by removal of the LCD 6 and utilising an alternative way of directing the light from laser 2, a more efficient system may be realised.

With some such systems it may also be desirable to remove the beam expander and condenser, as will be appreciated. In the example of FIG. 2, however, these components remain.

Because the LCD 6 has been removed, an alternative way of directing the light from the laser 2 which ultimately is received by the endoscope 12 is necessary. This may be achieved in any of a number of ways. Deflection of the beam from laser 2, possibly together with direct control of the intensity thereof and/or control of the deflection rate may be used to control the amount of light supplied to specific parts of the treatment area 22. In the embodiment of FIG. 2 deflection of the beam from laser 2 is achievable in the x and y axes by means of a galvanometer mirror assembly 32. Hence the ray 16 will impinge upon endoscope 12 at its proximal end adjacent lens 18 at an area which depends upon the deflection imparted thereto by the galvanometer mirror assembly 32.

The galvanometer mirror assembly 32 may be supplemented by an intensity modulation means such as Kerr Cell, Pockels Cell or LCD Shutter 34 which time-dependently attenuates the beam from laser 2. It will be appreciated that the galvanometer mirror assembly 32 is preferably situated either directly optically adjacent the laser 2 at focus $F^1$ or at the further point of focus F in order to effectively deflect the beam of light therefrom. Furthermore, at the sacrifice of optical efficiency, the galvanometer mirror assembly 32 could be placed anywhere along the optical path of the system if so desired.

In the example described with reference to FIG. 2, the output of the image analysis computer 30 controls the galvanometer mirror assembly 32 and/or the shutter 34 in analogy to the LCD 6 in FIG. 1.

Practitioners in this art will realise that the cholesteric liquid crystal material may itself be a sheet of polymer to form the beam-splitter 10 or may be arranged to overlie a supporting structure or be sandwiched as a layer of cholesteric liquid crystal or cholesteric liquid crystal polymer between supporting structures.

It will be apparent that a further light source, preferably having a spectral distribution which does not produce phototoxicity in a suitable chemical at the treatment area 22, may be used to illuminate the treatment area 22 so that this area may be imaged in this light at point 24. In such a case the treatment light source 2 may be pulsed synchronously in anti-phase with the further light source to achieve good contrast in such imaging or allow the treatment area to be viewed or analysed in the absence of the treatment light.

Although the quarter wave retarder 35 may be removed, a less optically efficient apparatus will result. The retarder 35 whilst not being essential, therefore, is preferable.

Those skilled in the art will realise that the use of fluorescent dyes, as taught in the acknowledged prior art, may be usefully employed within the present invention; such dyes will, of course, be chosen to fluoresce when illuminated by the light reflected by the splitter 10. This can enhance the ease of discriminating the unwanted growth from surrounding tissue and facilitate the operation of the image analysis computer. Alternatively or additionally it allows the use of treatment light having wavelengths which do not directly create a phototoxic effect, this light instead being absorbed by a suitable fluorescent dye which is concentrated in the growth, the dye then locally emitting light of wavelengths suitable to create this phototoxic effect in the treatment material also concentrated in the growth. This implementation gives a double degree of discrimination between the growth and surrounding or underlying healthy tissue.

Although in the above examples light from a discrete light source is subsequently appropriately directed it will be understood that an alternative is possible. More particularly the laser 2 and LCD 6 of FIG. 1 may, for example, be replaced by a cathode ray tube arranged to provide a raster or matrix-array type output. In this case, the pixels of phosphor on the optically-active surface of the tube will act both as the light source and be modulated by the supply of appropriate signals to the control electrode of the tube to control the area of emission and hence the area of the endoscope image surface 13 to which light is ultimately directed.

Whilst in the above description, the invention is described with reference to the supply of light to a treatment area, it will be apparent that an apparatus in accordance with the present invention may suitably be employed to supply a pattern of light to any area. For example areas inaccessible to humans such as confined spaces or the like may be illuminated and viewed using the present invention.

I claim:

1. A system for irradiating a treatment area with a controllable pattern of light, comprising an endoscope having first and second image surfaces, and an illumination system being arranged to selectively illuminate said first image surface, the illumination system comprising a light source, means for variably controlling the area of light falling upon said first image surface from said light source to selectively illuminate a given area of said first image surface said means being provided in a path of light from said light source to said first image surface, and a beam spitter being provided in said path between said source and said first image surface, the said beam spitter being arranged at an oblique angle to said path to divert away from said path at least a portion of any light returning along said path from said first image surface and comprising a sheet of cholesteric liquid crystal material for reflecting at least a portion of light from the source to said first image surface and transmitting at least a portion of any light returning from said first image surface, the said endoscope being constructed to relay an image from said first to said second image surface, and from said second image surface to said first image surface.

2. A system as claimed in claim 1 in which the light source is a source of linearly polarized light and the illumination system includes means for converting the light from the source to circular polarization prior to its incidence on the beam spitter.

3. A system for irradiating a treatment area with a controllable pattern of light, comprising an endoscope having first and second image surfaces, and an illumination system being arranged to selectively illuminate said first image surface, the illumination system comprising a light source, means for variably controlling the area of light falling upon said first image surface from said light source to selectively illuminate a given area of said first image surface said means being provided in a path of light from said light source to said first image surface and comprising a spatial light modulator comprising a matrix of pixels, each pixel being individually variable between a first and a second light transmissive state, said system further comprising a beam spitter being provided in said path between said source and said first image surface, the said beam spitter being arranged at an oblique angle to said path to divert away from said path at least a portion of any light returning along said path from said first image surface, the said endoscope being constructed to relay an image from said first to said second image surface, and from aid second image surface to said first image surface.

4. A system as claimed in claim 3 including an optical expander in said path between the light source and the spatial light modulator, and an optical condenser in said path between the spatial light modulator and the beam spitter.

5. A system as claimed in claim 3 in which the first transmission state is a state in which a given pixel permits transmission of light therethrough, and the second transmission state is a state in which the given pixel prevents transmission of light therethrough.

6. A system as claimed in claim 3 in which the first transmission state is a state in which a given pixel imparts a first sense of polarization to light being transmitted therethrough, and the second transmission state is a state in which the pixel imparts a second sense polarization to light being transmitted therethrough.

7. A system as claimed in claim 1 including imaging means positioned to receive light returning from said first imaging surface which is diverted out of said path by said beam spitter.

8. A system as claimed in claim 7 including control means having an input coupled to the imaging means and an output coupled to said illumination system for controlling the given area onto which the light is selectively directed in dependence upon the output of the imaging means.

9. A system as claimed in claim 1 in which the light source is a laser.

* * * * *